United States Patent [19]

Boberg et al.

[11] Patent Number: 4,782,162
[45] Date of Patent: Nov. 1, 1988

[54] NOVEL INTERMEDIATES FOR THE SYNTHESIS OF CEPHALOSPORINS

[75] Inventors: Michael Boberg; Paul Naab; Samir Samaan, all of Wuppertal, Fed. Rep. of Germany

[73] Assignee: Bayer Aktiengesellschaft, Leverkusen, Fed. Rep. of Germany

[21] Appl. No.: 872,304

[22] Filed: Jun. 9, 1986

Related U.S. Application Data

[62] Division of Ser. No. 731,235, May 6, 1985, abandoned.

[30] Foreign Application Priority Data

May 17, 1984 [DE] Fed. Rep. of Germany ....... 3418376

[51] Int. Cl.$^4$ ............................................ C07D 277/46
[52] U.S. Cl. ...................................... 548/195; 548/194
[58] Field of Search .......................................... 548/195

[56] References Cited

U.S. PATENT DOCUMENTS 4,203,899  5/1980  Ochiai .................... 548/195
4,278,793  7/1981  Durckheimer et al. ............ 548/194

FOREIGN PATENT DOCUMENTS 3145727  5/1983  Fed. Rep. of Germany .
6034957  8/1983  Japan ................................. 548/194

OTHER PUBLICATIONS

Boberg et al., *Chemical Abstracts*, vol. 100: 174,531x, 1984.
Kinast et al., *Chemical Abstracts*, vol. 101: 23231u, 1985.
Sagami Chemical, *Chemical Abstracts*, vol. 100: 121053m, 1984.

*Primary Examiner*—Robert Gerstl
*Attorney, Agent, or Firm*—Sprung Horn Kramer & Woods

[57] ABSTRACT

The new compounds of the formula

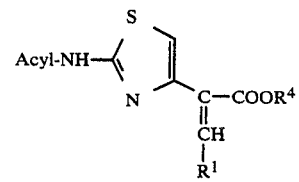

in which
Acyl is alkylcarbonyl optionally substituted by halogen or aryl, or arylcarbonyl, which is substituted by lower alkoxy, halogen or nitro,
$R^1$ is an alkyl or alkenyl radical, and
$R^4$ is an optionally substituted branched or straight-chain $C_1$–$C_6$-alkyl radical or a cycloalkyl radical, are produced by reacting a 2-halogenoacetylacrylic acid ester of the formula

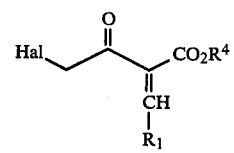

with an acylthiourea of the formula

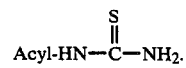

The reaction can be conducted in aqueous DMF, substantially pure Z-isomer selectively crystallizing out.

6 Claims, No Drawings

NOVEL INTERMEDIATES FOR THE SYNTHESIS OF CEPHALOSPORINS

This is a division, of application Ser. No. 731,235, filed May 6, 1985, now abandoned.

The invention relates to new alkyl 2-(2-acylamido-thiazol-4-yl)-2-butenoates, a process for their preparation and their use for the preparation of cephalosporins.

Cephalosporins of the general formula I are known from European Patent Application No. 49,448. These compounds have a broad antibacterial action both against Gram-negative and against Gram-positive bacteria.

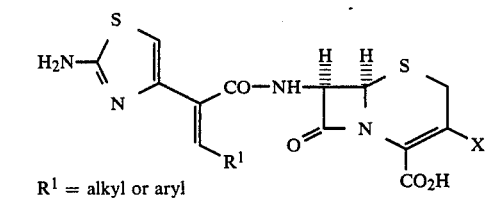

$R^1$ = alkyl or aryl

The compounds of the formula I are prepared by the process mentioned in this Patent Application by the method shown in the following equation:

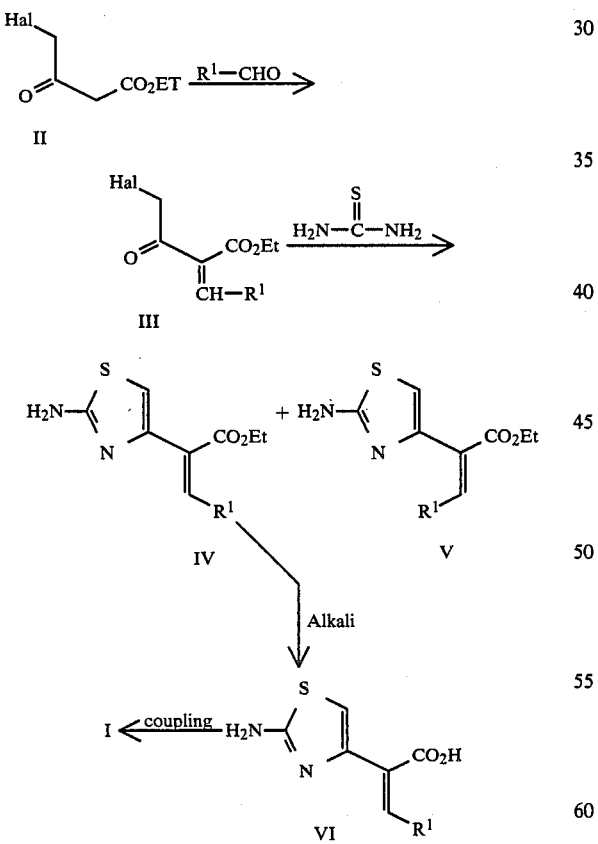

However, this process gives only unsatisfactory yields of compounds of the formula I where $R^1$=alkyl. Thus—for example in the case where $R^1$=isopropyl—the reaction of III with thiourea gives, by deconjugation of the double bond and by Michael addition, the products of the formulae VII and VIII in by far the highest amount, in addition to the Z-configurated compound IV and the E-configurated compound V.

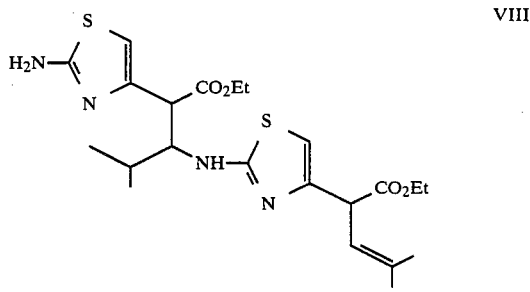

Furthermore, European Patent Application No. 81,674 describes a process for the preparation of compounds of the formulae XIII and XIV which can be used if $R^1$=alkyl and $R^1$=aryl and proceeds in accordance with the following equation:

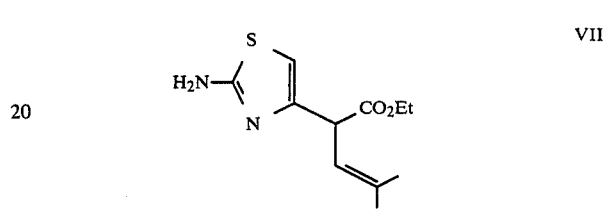

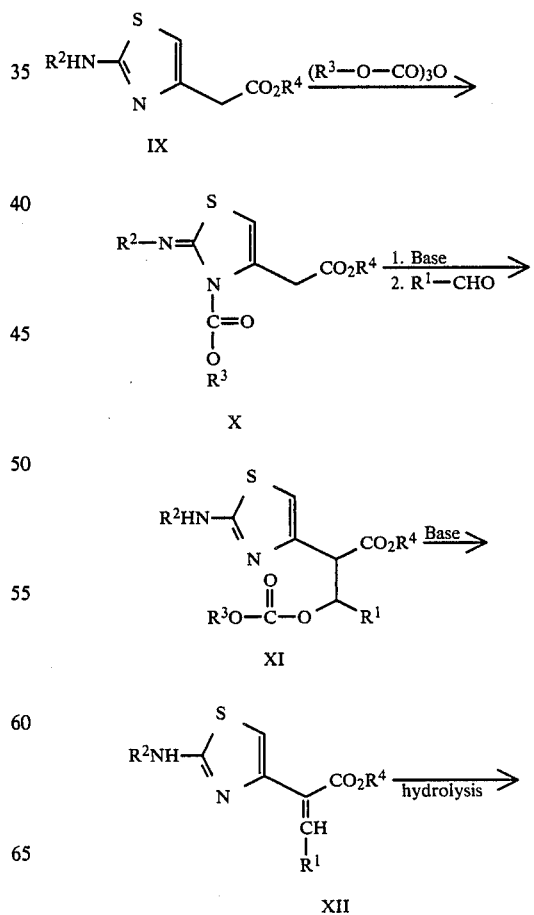

-continued

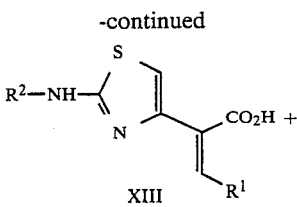

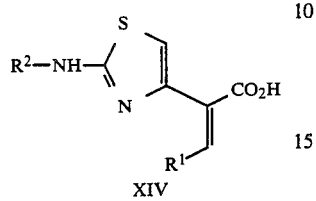

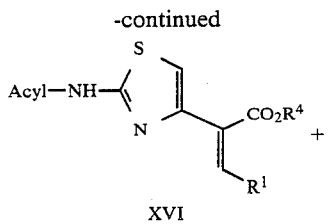

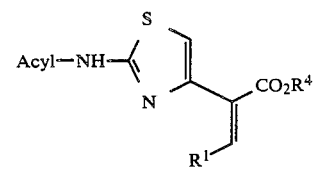

Although the required compound VI can be prepared in principle from XIII by splitting off the protective group $R^2$, as a result of the introduction and later splitting off of the two amino-protective groups $R^2$ and $COOR^3$, the preparation of VI requires more synthesis stages than the process described above, in addition to the separate splitting of the ester $CO_2R^4$ to give the carboxylic acid.

A process has now been found for the preparation of the preferred Z-configurated compound VI in which $R^1$=alkyl, alkenyl, cycloalkyl or cycloalkenyl, which gives purer products in only a few synthesis stages via the new intermediates of the formulase XVI and/or XVII.

Surprisingly, it has been found that if the 2-halogenoacetylacrylic acid esters III are reacted with an acylthiourea XV, preferably acetylthiourea, instead of with thiourea, the compounds XVI and XVII are formed in a higher purity and are very easy to isolate.

Acylthioureas which are suitable for the reaction have the formula XV

wherein
acyl represents alkylcarbonyl, preferably $C_1$-$C_6$-alkylcarbonyl, it being possible for the alkyl to be branched, straight-chain or cyclic and substituted by halogen or aryl, and if by aryl, then preferably by phenyl, arylcarbonyl, preferably phenylcarbonyl, or phenylcarbonyl which is substituted by lower alkoxy, halogen or nitro.

The preparation of the intermediates XVI and XVII proceeds in accordance with the following equation:

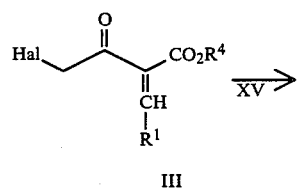

In this equation
acyl denotes the radicals mentioned in the case of XV,
$R^1$ denotes an optionally substituted, branched or straight-chain alkyl, alkenyl, cycloalkyl or cycloalkenyl radical and
$R^4$ denotes an optionally substituted, branched or straight-chain $C_1$-$C_6$-alkyl or cycloalkyl radical.

The invention accordingly relates to compounds of the formulae XVI and XVII

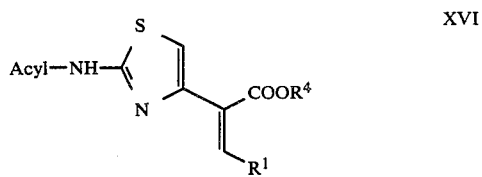

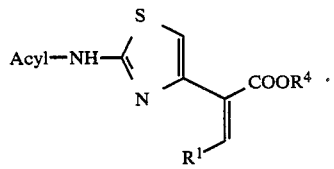

in which
acyl denotes the radicals mentioned in the case of XV,
$R^1$ denotes an optionally substituted, branched or straight-chain alkyl, alkenyl, cycloalkyl or cycloalkenyl radical and
$R^4$ denotes an optionally substituted, branched or straight-chain $C_1$-$C_6$-alkyl radical or a cycloalkyl radical.

Compounds of the formula XVI and XVII in which $R_1$ represents an optionally substituted, branched or straight-chain alkyl radical or alkenyl radical with up to 18 C atoms and in which acyl represents acetyl are preferred.

Compounds of the formulae XVI and XVII in which $R_1$ represents an optionally substituted, branched or straight-chain alkyl or alkenyl radical with up to 12 C atoms, in particular up to 6 C atoms, and in which acyl represents acetyl are furthermore particularly preferred.

$R_1$ and $R_4$ can also represent a cycloalkyl or cycloalkenyl radical with up to 6 C atoms.

The process for the preparation of the compounds with the formulae XVI and XVII comprises reaction of 2-halogenoacetylacrylic acid esters of the formula III

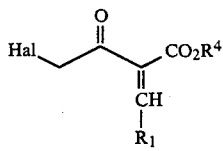

in which
R¹ denotes an optionally substituted, branched or straight-chain alkyl, alkenyl, cycloalkyl or cycloalkenyl radical, and
R₄ denotes an optionally substituted, branched or straight-chain $C_1$–$C_6$-alkyl radical or a cycloalkyl radical, with an acylthiourea of the formula XV, preferably with acetylthiourea.

The reaction of III with XV can be carried out in a polar solvent, such as, for example, acetonitrile, acetone, dimethylformamide or dimethyl sulphoxide, or in a polar solvent containing hydroxyl groups, such as, for example, methanol, ethanol or water, or in a solvent mixture, such as, for example, ethanol/water or dimethylformamide/water, in a temperature range between 20° C. and 150° C., preferably between 60° C. and 90° C. After the reaction has been carried out and the reaction solution has cooled, the preferred products XVI and XVII can be isolated by direct crystallization from the reaction mixture.

It has furthermore been found that, by appropriate choice of the reaction conditions, this reaction can be controlled so that, after reaction of an isomer mixture III with XV, only the preferred Z-isomeric reaction product XVI crystallizes out, in pure isomer form. A mixture of dimethylformamide and water containing up to 80%, preferably 30 to 50%, of water is preferably used as the reaction medium here.

It has furthermore been found that the products VI and XVIII can be prepared in one step from the compounds of the formulae XVI and XVII by simultaneous alkaline cleavage of the amide and the ester group $COOR^4$.

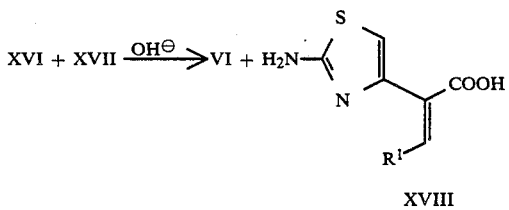

A mixture of VI and XVIII can be prepared here from a mixture of XVI and XVII. By choosing a suitable acyl radical, a suitable radical R₄ and suitable reaction conditions, it is moreover possible to synthezise the pure particularly preferred compound VI stereospecifically from the pure compound XVI and the pure compound XVIII stereospecifically from the pure compound XVII. Examples of suitable radicals R⁴ are methyl and ethyl. Particularly suitable solvents for this step are protic solvents or solvent mixtures, such as, for example, ethanol/water, methanol/water or water, and alkali metal hydroxides, such as lithium hydroxide, sodium hydroxide or, advantageously, potassium hydroxide can be used as the alkaline reagent. The reaction proceeds at room temperature, preferaly at elevated temperatures, in the course of 1 to 24 hours. It is particularly advantageous for the process to carry out the reaction at temperatures between 60° C. and 100° C. It is furthermore advantageous to use a 2- to 10-fold, preferably a 2- to 5-fold, molar excess of the alkali metal hydroxide, in particular as a 1 to 6 molar solution. After the reaction has been carried out, the products VI and/or XVIII are precipitated in a high purity at pH 3 to 4 by acidification of the reaction solution with, for example, concentrated hydrochloric acid or trifluoroacetic acid.

It has furthermore been found that it is possible selectively to cleave the ester group $CO_2R^4$ in the compounds XVI and XVII, the amide structure being retained, to give the carboxylic acids XIX and XX, in which acyl has the abovementioned meaning.

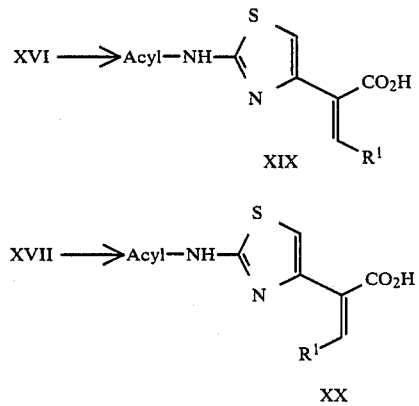

Compounds of the formulae XIX and XX in which acyl represents acetyl are preferred.

The compounds XIX and XX can be used as intermediates for cephalosporin syntheses, but they can also be cleaved in a reaction analogous to the reaction XVI→VI and XVII→XVIII described above, to give VI and XVIII respectively.

Solvents and bases which can be used for the reaction XVI→XIX and XVII→XX are those mentioned for the reaction XVI→VI and XVII→XVIII. It is advantageous here for the process if the reaction is carried out at room temperature in the course of 2 to 4 hours.

EXAMPLE 1

Ethyl 2-(2-acetamidothiazol-4-yl)-2-butenoate

A solution of 10.4 parts by weight of acetylthiourea and 16.4 parts by weight of ethyl 2-ethylidene-4-chloro-3-oxobutyrate in 40 parts by volume of N,N-dimethylformamide is warmed at 80° C. for 2 hours.

After cooling, the mixture is poured into 100 parts by volume of water, with stirring, and stirred for 10 minutes and the precipitate is filtered off with suction.

19.3 parts by weight of product are obtained.

NMR (CDCl₃): Z-isomer: δ=10.30 (1) s broad, 6.97 (1) s, 6.81 (1) q, J=7 Hz, 4.36 (2) q, J=7 Hz, 2.17 (3) s, 1.97 (3) d, J=7 Hz and 1.34 (3) t, J=7 Hz ppm. E-isomer: δ=10.60 (1) s broad, 7.16 (1) q, J=7 Hz, 6.92 (1) s, 4.20 (2) q, J=7 Hz, 2.13 (3) s, 1.87 (3) d, J=7 Hz and 1.20 (3) t, J=7 Hz ppm.

EXAMPLE 2

2-(2-Acetamidothiazol-4-yl)-2-butenoic acid 5 parts by weight of ethyl 2-(2-acetamidothiazol-4-yl)-2-butenoate are dissolved in 40 parts by volume of 2N sodium hydroxide solution at 10° C., with cooling. The solution is stirred at room temperature for 3.5 hours and then brought to pH 3.6 with 6N hydrochloric acid, while cooling with ice, and the mixture is then diluted, if necessary, with a little water and the product is filtered off with suction. The residue is washed with cold water and dried, and 3.6 parts by weight of pure product are obtained.

NMR (DMSO=$d_6$): E-isomer: $\delta$=7.01 (1) s, 6.90 (1) q, J=7 Hz, 2.10 (3) s and 1.82 (3) d, J=7 Hz ppm.

Z-isomer: $\delta$=6.93 (1) s, 6.42 (1) q, J=7 Hz, 2.12 (3) s and 1.86 (3) d, J=7 Hz ppm.

EXAMPLE 3

2-(2-Aminothiazol-4-yl)-2-butenoic acid 8.4 parts by weight and ethyl 2-(2-acetamidothiazol-4-yl)-2-butenoate are added to a solution, warmed to 90° C., of 18.8 parts by weight of potassium hydroxide in 168 parts by volume of water. The solution is stirred for 45 minutes at the same temperature, cooled and brought to pH 3.6 with concentrated hydrochloric acid, with cooling.

After 30 minutes, the mixture is filtered with suction to give 3.6 parts by weight of product.

EXAMPLE 4

Ethyl Z-2-(2-acetamidothiazol-4-yl)-2-butenoate 14.6 parts by weight of acetylthiourea, 30 parts by volume of water and 50 parts by volume of N,N-dimethylformamide are heated up to 85° C. under nitrogen. 22.9 parts by weight of ethyl 2-ethylidene-4-chloro-3-oxobutyrate are then added at this temperature in the course of 40 minutes. The mixture is stirred at 80° to 85° C. for 1 hour and then cooled to 15° C., and, after 10 minutes, the precipitate which has separated out is filtered off with suction. The precipitate is suspended once in 34.5 parts by volume of water, filtered off with suction again and washed twice more with water. The crude product is dried and then extracted by stirring once in a mixture of 13.8 parts by volume of water and 41.8 parts by volume of ethanol for 10 minutes, filtered off with suction and rinsed with ethanol/water (3/1). After drying, 8.8 parts by weight of a pure product are obtained.

EXAMPLE 5

Ethyl 2-ethylidene-4-chloro-3-oxobutyrate 0.25 part by weight of piperidine is added dropwise to a mixture of 32.9 parts by weight of ethyl 4-chloroacetoacetate and 9.6 parts by weight of acetaldehyde at −20° C. The mixture is left to stand at −20° C. for 5 to 6 hours and ice-cold 1N hydrochloric acid and ethyl acetate are then added. The ethyl acetate phase is separated off, extracted twice more with 1N hydrochloric acid and then once with water, dried over magnesium sulphate and concentrated. 35.6 parts by weight of a yellow oil are obtained, and are distilled using a bulb tube (oven temperature 80° to 110° C. under 0.07 mm). 15.5 parts by weight of product are obtained.

EXAMPLE 6

Ethyl Z-2-(2-acetamidothiazol-4-yl)-2-butenoate 208 parts by weight of acetylthiourea and 328 parts by weight of ethyl 2-ethylidene-4-chloro-3-oxobutyrate are dissolved in 800 parts by volume of N,N-dimethylformamide. The mixture is warmed at 85° C. for 2 hours, 2,000 parts by volume of water are added and the mixture is cooled to 20° C. The precipitate which has separated out is filtered off with suction, stirring twice with 1,200 parts by volume of ether each time for 15 minutes and filtered off with suction again. Recrystallization of the residue from a mixture of 100 parts by volume of ethanol and 400 parts by volume of water gives 130 parts by weight of pure product. Further product can be isolated as an E/Z mixture from the ethereal and ethanolic-aqueous mother liquors.

EXAMPLE 7

E-2-(2-Acetamidothiazol-4-yl)-2-butenoic acid 22 parts by weight of ethyl E-2-(2-acetamidothiazol-yl)-2-butenoate are added to a solution of 12 parts by weight of sodium hydroxide in 130 parts by volume of water. After the mixture has been stirred at 25° C. for 90 minutes, 750 parts by volume of water are added, while cooling with ice, and the pH is brought to 2.8 with 2N hydrochloric acid. The product precipitated is filtered off with suction, washed twice with 50 parts by volume of water each time and dried. 17.9 parts by weight of the title compound are obtained.

EXAMPLE 8

Ethyl 2-ethylidene-4-chloro-3-oxobutyrate 50 parts by weight of ethyl 4-chloroacetoacetate and 76 parts by volume of ethyl acetate are taken, covered with a layer of nitrogen and cooled to −75° C. 33 parts by weight of acetaldehyde are added to the cold solution and a solution of 0.43 part by volume of piperidine in 3 parts by volume of ethyl acetate is then allowed to run in over a period of 50 minutes. The solution is now warmed to 0° C. in the course of 40 minutes and is stirred at this temperature for 2 hours. After addition of 121 parts by volume of 1N hydrochloric acid and 16 parts by weight of sodium chloride, the mixture is worked up. The organic phase is separated off and the aqueous phase is extracted again with 45 parts by volume of ethyl acetate. The combined organic phases are extracted twice with a solution of in each case 16 parts by weight of sodium chloride in 55 parts by volume of water and dried. After the solvent has been stripped off, 51.9 parts by weight of product remain, which can be further processed in the crude form.

EXAMPLE 9

Z-2-(2-Aminothiazol-4-yl)-2-butenoic acid

A solution of 16.5 parts by weight of potassium hydroxide in 111 parts by volume of water is heated up to 75° to 78° C. 14.9 parts by weight of ethyl Z-2-(2-acetamidothiazol-4-yl)-2-butenoate are added and the mixture is stirred at 75° to 78° C. for 2 hours. After cooling to 10° C., the mixture is brought to pH 7.0 with trifluoroacetic acid, the solution is filtered with suction over kieselguhr and the pH is then brought to 3.6 with further trifluoroacetic acid. The mixture is cooled to 0° C. and stirred at 0° C. for 30 minutes, and the crystals which have precipitated are isolated. After washing three times with 6 parts by volume of isopropanol each time, the crystals are dried. The product is then stirred with 62.4 parts by volume of acetone for 20 minutes, filtered off with suction, washed with 42 parts by volume of acetone and dried again. 6.3 parts by weight of pure product are obtained. Further product can be isolated from the mother liquor of the acetone extraction stirring.

EXAMPLE 10

Ethyl Z-2-(2-acetamidothiazol-4-yl)-2-butenoate 150 parts by weight of ethyl 4-chloroacetoacetate are dissolved in 250 parts by weight of methylene chloride in a three-necked flask with a stirrer, reflux condenser, thermometer and dropping funnel and the solution is cooled to 10° C. 100 parts by weight of acetaldehyde are added all at once. A solution of 1.38 parts by volume of piperidine in 25 parts by volume of methylene chloride is then added dropwise at 10° C., with stirring, such that the internal temperature is kept between 10° and 20° C. When the dropwise addition has ended, the mixture is subsequently stirred at 20° C. for 1.5 hours. 107.6 parts by weight of acetylthiourea, 225 parts by volume of dimethylformamide and 125 parts by volume of water are then added to the batch and a distillation head/condenser is attached. The mixture is heated on a bath warmed to 80° C. When no further material distils over and the internal temperature has reached the 80° C. level, the mixture is subsequently stirred at 80° C. and then cooled to 10° to 15° C. The mixture is stirred at 10° to 15° C. for 30 minutes and the precipitate is filtered off with suction, rinsed with the mother liquor and sucked dry. The product which has been sucked dry is rinsed three times with 90 parts by volume of water each time and dried. The crude product is stirred with 241 ml of ethanol/water (3:1), filtered off with suction, washed with ethanol/water (3:1) and dried. 52.3 parts by weight of pure product are obtained.

It will be understood that the specification and examples are illustrative but not limitative of the present invention and that other embodiments within the spirit and scope of the invention will suggest themselves to those skilled in the art.

We claim:

1. A process for preparation of a compound of the formula

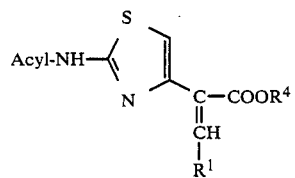

in which
acyl is alkylcarbonyl unsubstituted or substituted by halogen or aryl, or arylcarbonyl which is substituted by lower alkoxy, halogen or nitro,
$R^1$ is an alkyl, alkenyl, cycloalkyl or cycloalkenyl radical, and
$R^4$ is an unsubstituted or substituted, branched or straight-chain $C_1$–$C_6$-alkyl radical or a cycloalkyl radical,
comprising reacting a 2-halogenoacetylacrylic acid ester of the formula

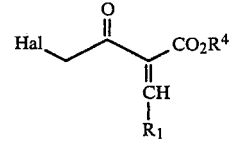

with an acylthiourea of the formula

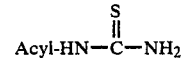

in a dimethylformamide/water mixture which contains 30 to 50% water at a temperature from about 20° to 150° C., and the reaction medium is thereafter diluted with water and cooled, thereby crystallizing out substantially pure Z-isomer.

2. A process according to claim 1, wherein the acylthiourea is acetylthiourea.

3. A process according to claim 1, wherein the temperature is 60° C. to 90° C.

4. A process according to claim 1, wherein $R^1$ is an alkyl or alkenyl radical with up to 18 C atoms, and Acyl is acetyl.

5. A process according to claim 1, wherein $R^1$ is an unsubstituted or substituted, branched or straight-chain alkyl or alkenyl radical with up to 12 C atoms.

6. A process according to claim 1, wherein $R^1$ and $R^4$ each independently is a cycloalkyl or cycloalkenyl radical with up to 6 C atoms.

* * * * *